United States Patent [19]

Chang

[11] Patent Number: 5,872,222
[45] Date of Patent: Feb. 16, 1999

[54] CONJUGATES OF POLYMERS AND ANTIBODIES SPECIFIC FOR T LYMPHOCYTES, AND THEIR USE AS ADJUVANTS

[75] Inventor: Tse Wen Chang, Houston, Tex.

[73] Assignee: Tanox Biosystems, Inc., Houston, Tex.

[21] Appl. No.: 993,291

[22] Filed: Dec. 18, 1992

Related U.S. Application Data

[63] Continuation-in-part of Ser. No. 926,566, Aug. 6, 1992, abandoned, and Ser. No. 819,449, Jan. 10, 1992, abandoned, which is a continuation-in-part of Ser. No. 688,000, Apr. 19, 1991, abandoned.

[51] Int. Cl.[6] .................................................... C07K 16/00
[52] U.S. Cl. .................................. 530/391.1; 530/389.6; 530/388.75
[58] Field of Search ...................... 424/85.8; 530/391.1, 530/389.6, 388.75

[56] References Cited

FOREIGN PATENT DOCUMENTS

| | | |
|---|---|---|
| 3242389 | 5/1989 | Australia . |
| 6623590 | 5/1991 | Australia . |
| 0336379 | 4/1989 | European Pat. Off. . |
| WO8912458 | 12/1989 | WIPO . |
| WO9006758 | 6/1990 | WIPO . |
| WO9013281 | 11/1990 | WIPO . |
| WO9013316 | 11/1990 | WIPO . |
| WO9103493 | 3/1991 | WIPO . |
| WO9206193 | 4/1992 | WIPO . |
| WO9207878 | 5/1992 | WIPO . |
| WO9213562 | 8/1992 | WIPO . |

OTHER PUBLICATIONS

Paul *Fundamental Immunology* Raven Press (1989) p. 364.
Verwilghen et al Immunology 72:269–276 1991.
Geppert et al, 138:1660–1666, 1987, Journal of Immunology.
Williams et al, 135:2249–2255, 1985, J. Immunol.
Edgington Bio/Technology 11:1117–1119 1993.
Ellenhorn et al. J.I. 144:2840–2846 1990.
Ellenhorn et al. Science 242 :569–571 1988.
Hirsch et al. J.I. 147:2088–2093 1991.
Ceuppens et al. J.I. 137:1816–1821 1986.

*Primary Examiner*—Frank C. Eisenschenk
*Attorney, Agent, or Firm*—Eric P. Mirabel

[57] ABSTRACT

Disclosed are conjugates including a substantially nonimmunogenic polymer backbone or microbead and binding molecules, such as Fv, Fab, or F(ab')$_2$ fragments of monoclonal antibodies or whole antibodies that are bound through their Fc carbohydrate moieties or have their Fc portion modified so that they cannot effect ADCC or complement-mediated cytolysis, and that are specific for a T cell surface antigen, such as CD3, TCR, CD4, CD8, or CD28 on T cells. The polymer or microbead is preferably made of cross-linked dextran, ficoll, latex, or agarose, and is preferably of 0.1 to 10 μm in size, so that it can be suspended in fluids for in vivo applications. These conjugates can be used as adjuvants to enhance the antibody response against an administered immunogen.

7 Claims, 1 Drawing Sheet

CONJUGATES OF POLYMERS AND ANTIBODIES SPECIFIC FOR T LYMPHOCYTES, AND THEIR USE AS ADJUVANTS

RELATED APPLICATIONS

This application is a continuation-in-part of U.S. application Ser. No. 07/926,566, filed Aug. 6, 1992 (abandoned) and U.S. application Ser. No. 07/819,449, filed Jan. 10, 1992 (abandoned), which is a continuation-in-part of U.S. application Ser. No. 07/688,000, filed Apr. 19, 1991 (abandoned).

FIELD OF INVENTION

The invention relates to immunoconjugates for use as adjuvants for enhancing the immune response in laboratory animals, in order to aid in production of antibody reagents and monoclonal antibodies.

BACKGROUND OF THE INVENTION

Because antibodies specific for a large variety of biological substances can be prepared, polyclonal antibodies produced in rabbits, goats, or sheep have been very important reagents in all disciplines of biomedical research and in medical diagnostics. These antibodies are the essential components in various kinds of immunoassays, such as radio-immunoassays and enzyme-linked immunosorbent assays.

In the past 10–15 years, the development of monoclonal antibody methodologies has further enhanced the importance of antibody reagents in biomedical research medical diagnostics. These monoclonal antibodies (MAbs) have additional utilities in in vivo diagnostics and therapies.

In producing MAbs in mice, the first step is to inoculate the mice with the immunogen which one wishes to make monoclonal antibodies against. Thereafter, following a well-known procedure, one fuses B cells from the mouse spleen with a tumorous B cell line (myeloma cell line) to create immortal hybridoma cell lines, and then screens and identifies the hybridomas which produce the monoclonal antibodies of interest. The screening of these hybridomas is typically done by determining the specific reactivity of the antibodies secreted by the hybridomas with the immunogen, or a peptide representing the epitope of the immunogen which is of interest.

Many immunogens are not capable of triggering an adequate antibody response in the mice. This means that there are only few B cells producing antibody against the immunogen, making it difficult to isolate these cell lines after forming hybridomas. The low antibody response results because the immunogens do not elicit adequate T cell help to expand B cell clones specific for the antigen to an appreciable extent.

Thus, one often uses adjuvants which cause an enhanced antibody response against an immunogen, in order to increase the number of B cells which produce antibody against the immunogen. One potent adjuvant which is often used for priming a response is Freund's complete adjuvant ("CFA"). CFA is a mixture of oil (Bayol F) and detergent (mannide monooleate) containing Mycobacterium tuberculosis. CFA is administered in a mixture together with the immunogen. There is a need to investigate new adjuvants, however, because regulatory agencies discourage use of CFA in laboratory animals, due to its serious side effects.

This application is directed to adjuvants which are conjugates of polymers and binding molecules which target surface antigens on T cells, preferably CD3 or other components of the T cell antigen receptor. Binding molecules are antibodies, antibody fragments, single chain antibodies, and peptides which are capable of receptor binding. Such adjuvants have never been disclosed or suggested, as discussed below.

A number of MAbs specific for CD3 on the surface of human T cells (pan T markers) are known to be very potent mitogens of human T cells in vitro, e.g., the MAb OKT3, Van Wauwe, J. P. et al., *J. Immunology* 124:2708 (1980); Chang, T. W. et al., *Proc. Natl. Acad. Sci. U.S.A.* 78:1805 (1981); MAb 64.1 Hansen, J. A. et al., *Leukocyte Typing: Human Leukocyte Differentiation Antigens Detected by Monoclonal Antibodies*, Eds. Bernard, A. et al. (Spring Verlag, N.Y., 1984). In medium containing only fetal calf serum and no human serum (and therefore no IgG), the anti-CD3 MAbs are much more potent than phytohemagglutinin A ("PHA") or Concanavalin A ("Con A") in inducing T cell proliferation.

But the mitogenic effect of anti-CD3 requires both specific binding to the CD3 antigen and the presence of the Fc moiety of the antibody, as well as the presence of monocytes and macrophages. The best explanation for these results is that the Fc of the anti-CD3 MAbs binds to the Fc receptors on monocytes/macrophages, thereby aggregating the CD3 antigen and the T cell receptor (CD3/TCR) on the T cell surface, which triggers the activation and proliferation of the T cells.

This explanation is supported by experiments which show that when the anti-human CD3 MAb is conjugated to Sepharose 4B beads or coated on the substratum plastic surface of culture wells, monocytes and macrophages are not needed to induce activation and proliferation of T cells. See Williams, J. M. et al., *J. Immunol.* 135:2249 (1985); Ceuppens, J. L. & Baroja, M. L., *J. Immunol.* 137:1816 (1986); Geppert, T. D. & Lipsky P. E., *J. Immunol.* 138:1660 (1987). Based on these experiments, it has been suggested that the solid-phase anti-CD3 MAb functions by aggregating the CD3/TCR complexes on the T cell surface.

However, when anti-human CD3 is injected in vivo, the results are the opposite of the in vitro effects. OKT3 MAb, which is the first MAb ever approved for therapeutic use in vivo, is strongly immunosuppressive and is approved for use as an immunosuppressant for patients receiving kidney transplants. Ortho Multicenter Group Study, *N. Eng. J. Med.* 313:337 (1985). The injection of OKT3 causes rapid depletion of T cells from the circulation.

Administration of anti-CD3 monoclonal antibodies (or F(ab')$_2$ fragments thereof) to mice also causes T cell depletion. Hirsch, R. et al., *Transplantation* 49:1117–23 (1990). This monoclonal antibody also caused weight loss, diarrhea, and decreased activity within 24 hours in all mice, and death of one-half of the mice it was administered to in 3 days. Hirsch, R. et al., id. at p. 1118, col. 1, paragraph 2. In another study it was observed that mice administered 40 μg of this anti-CD3 antibody seemed to develop more rapidly growing tumors. Ellenhorn, J. D. et al., *Science* 242:569–571 (1988) at p. 570, in the legend of FIG. 3. These observations are consistent with the observation that this antibody caused depletion of T cells and immunosuppression.

Although the mechanism by which anti-CD3 causes this rapid depletion of T cells is not well understood, the best explanation is that anti-CD3 induces antibody-dependent cellular cytotoxicity ("ADCC") of the T cells, i.e., as the T cells coated by anti-CD3 circulate through the spleen and liver, they are lysed by the phagocytic cells of the reticuloendothelial system in these organs. It is also possible that some of the T cells are destroyed by complement-mediated cytolysis and some other cytolytic mechanisms.

Thus, the studies all indicate that anti-CD3 binding molecules will cause depletion of T cells in vivo. Depletion of T cells causes a generalized immunosuppression, and does not lead to an increase in the number of antibody-producing B cells. Accordingly, one would expect that anti-CD3 binding molecules would not act as effective adjuvants for aiding in producing antibodies.

SUMMARY OF THE INVENTION

The immunoregulatory substances of the invention are conjugates which include a substantially nonimmunogenic polymer, such as latex, polyethylene glycol ("PEG"), cellulose, dextran, ficoll, agarose, an amino acid copolymer, a liposome, or a microbead that is coupled with a plurality of binding molecules, for example, antibodies or antibody-derived fragments, e.g., Fv, Fab, or F(ab')$_2$, which bind to surface antigens of human T lymphocytes, and which have immunoregulatory activities in vivo, when administered according to the techniques of the invention. Examples include anti-CD3 and anti-CD4, which have both been found to have stimulatory effects in vitro. A number of studies have indicated that the activation of T cells with an anti-CD3 MAb can be enhanced by an MAb which is specific for a different surface antigen on T cells. These auxiliary MAbs include those specific for HLA class-1 antigens, HLA class-II antigens (such as Ia), CD2, CD4, CD5, CD8, CD28, or CD37, all of which could also be formulated into immunoconjugates of the invention. The binding molecules all either lack an Fc portion or have a modified Fc portion, or are bound to the polymer backbone or microbead in such a way that the binding molecule is substantially ineffective in mediating antibody-dependent cellular cytotoxicity or complement-mediated cytolysis of T cells. The binding molecules can also be of other isotypes, such as IgA or IgE, or of the human IgG2 or IgG4 subclass, as these isotypes and subclasses do not cause ADCC or fix complement. The intended use of these immunoregulatory substances is as adjuvants for immunogens, to aid in making antibodies against the immunogens.

In one embodiment, the invention includes a polymer backbone or base to which binding molecules may be conjugated. The backbone may be latex, PEG, cellulose, dextran, ficoll, agarose or other polymers. Active groups for cross-linking may be introduced by established methods. Alternatively, long chain peptides containing Lys or Cys residues may be synthesized. A preferred family of amino acid copolymers are synthesized by a routine method, containing Gly, Ser, and Lys (or Cys) at 20:4:1 ratio, with molecular weights of 10,000 to 1,000,000 (about 150 to 15,000 amino acid residues long). Liposomes or microbeads formed by cross-linked polymers such as latex, dextran or agarose, may also be used as the base for conjugating antibody fragments. These liposomes and microbeads are preferably about 0.1 to 10 $\mu$m in diameter and can be suspended homogeneously in a liquid medium by agitation.

PEG has been used to modify single protein molecules for enhancing the serum half lives (reducing the clearance rate) and for reducing the immunogenicity of the proteins. In such an application, several PEG molecules, usually of small sizes (mw 1,000–4,000), are coupled to each protein molecules.

In the present invention, the PEG molecules provide the backbone or matrix for the coupling of a large number of protein molecules. The PEG molecules are formed by the cross-linking of a large number of small PEG molecules. These cross-linked PEG molecules are large enough to provide coupling sites (after activation) for a large number of protein molecules.

DETAILED DESCRIPTION OF MAKING AND USING THE INVENTION

Figure 1:
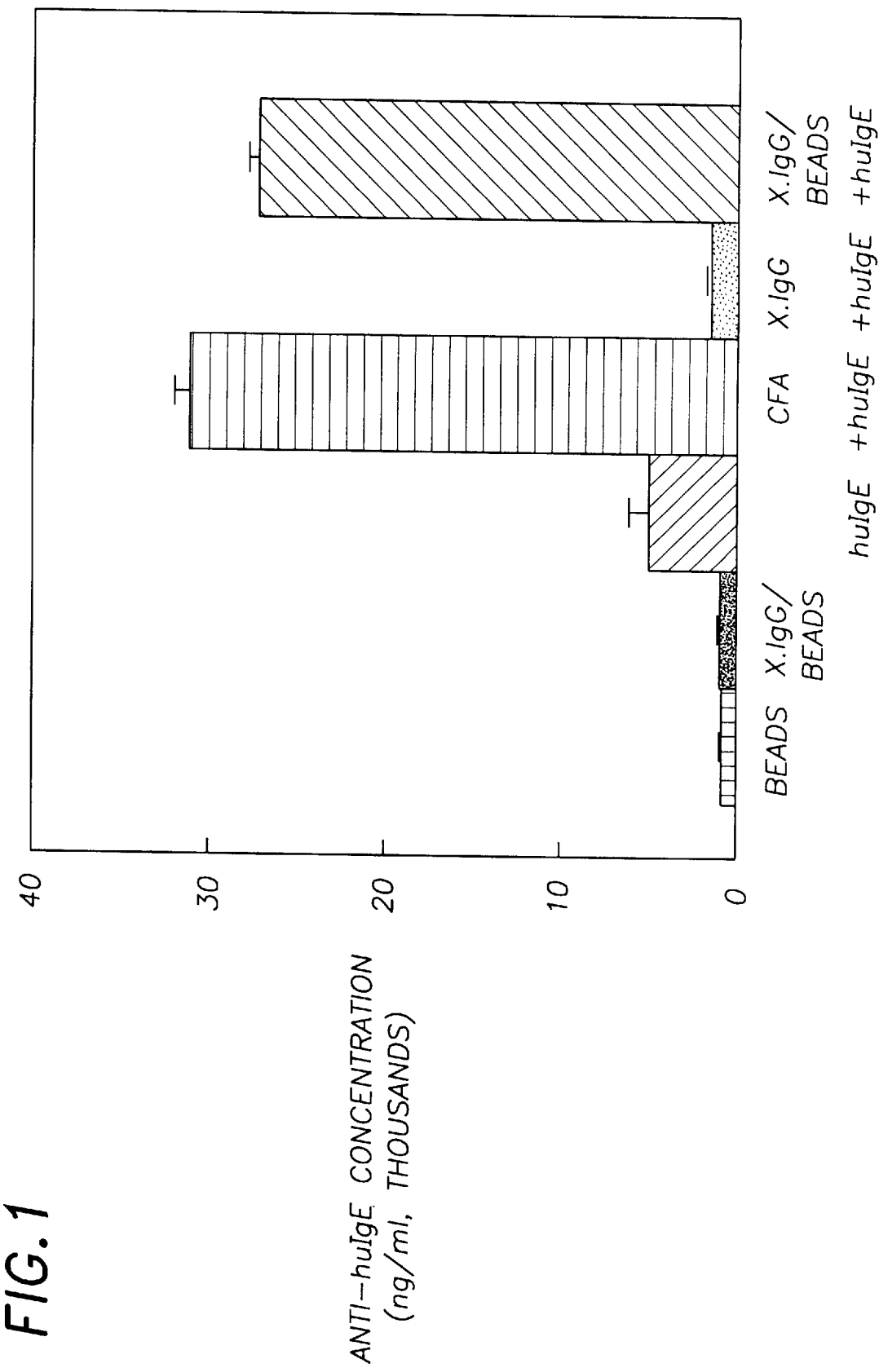
FIG. 1 is a bar graph showing the antibody response of mice injected with the various formulations indicated on the X axis.

The conjugates of the invention include binding molecules which target CD3, such as the monoclonal antibodies OKT3 (Ortho Diagnostic Systems, Raritan, N.J.), or the monoclonal antibody 64.1 (Hansen, J. A. et al., "Leukocyte Typing, ed. Bernard, A. et al., Springer-Verlag Pulications, Berlin 1984), which has a higher affinity for CD3 than OKT3. Other binding molecules specific for CD3 can be made by standard techniques, using either whole T cells or peptides representing the CD3 surface antigen as the immunogen.

Fv fragments of the anti-CD3 MAbs may be produced in bacteria using single chain antibody technology, as described in U.S. Pat. No. 4,946,778 and International Application No. WO88/09344. The Fv may also be genetically engineered to contain glycosylation sites and produced in mammalian cells, to result in a fragment containing carbohydrate moieties. The amino acid sequences that are targets for post-translational glycosylation modifications of proteins are known. Marshall, R. D. and Neuberger, A. Glycoproteins, ed. Gottschalk, A. (Elsevier, Amsterdam, 1972).

Fab or F(ab')$_2$ may be produced by enzymatic cleavage of whole IgG which is produced by a hybridoma or a transfected cell lines (a myeloma or a cell line such as CHO), using pepsin and papain digestion, respectively.

The binding molecules can be conjugated to the linear or cross-linked backbone of a liposome using conventional techniques. See, e.g., Ostro, M. J. (Ed.), *Liposomes: from Biophysics to Therapeutics* (Marcel Dekker, New York, 1987). One preferred method of preparing liposomes and conjugating immunoglobulins to their surface is described by Ishimoto, Y. et al., *J. Immunol. Met.* 75:351 (1984). Multilamillar liposomes composed of dipalmitoylphosphatidylcholine, cholesterol and phosphotidylethanolamine are prepared. Purified fragments can then be coupled to the phosphatidylethanolamine by the cross-linking agent N-hydroxysuccinimidyl 3-(2-pyridyldithio) propionate. The coupling of the binding molecule to the liposome can be demonstrated by the release of a pre-trapped marker, e.g., carboxyfluorescence, from the liposomes upon the treatment of secondary antibody against the conjugated fragment and complement. Liposomes have different sizes, ranging from 0.1 to 5 $\mu$m in diameter.

The binding molecules may also be coupled to polymerized microbeads. These microbeads are preferably about 0.1 to 10 $\mu$m in diameter (i.e., equal to or smaller than the diameter of resting blood lymphocytes), which allows them to be suspended in a liquid medium suitable for pharmaceutical administration in vivo. When agitated, the microbead suspension remains homogenous for at least several minutes, allowing time for withdrawal of the suspension and administration of it to a patient. The Sepharose 4B beads used for immobilizing anti-CD3 antibodies for in vitro studies of T cell activation (Williams, J. M. et. al., *J.*

*Immunol.* 135:2249 (1985)) are about 45–165 μm in diameter. These large Sepharose 4B beads settle readily, and do not remain suspended for a sufficient period to allow withdrawal and administration of a homogenous suspension. Also, the beads are so large that they can not pass through the bore of needles of smaller diameters (or higher gauge numbers), and, when injected i.v., they may not pass capillaries and may block blood flow in tissues. For in vivo administration, the preferred microbeads should be stable for relatively long periods. Such microbeads include those made by cross-linking, in a well-established manner, latex, agarose or dextran, one example of which is Superose 12 (Pharmacia LKB Biotechnology, Piscataway, N.J. 08854), and another example of which is glutaraldehyde modified latex beads (Interfacial Dynamics Corporation, Portland, Oreg.).

The binding molecules may be coupled to the liposome, the microbead, or another carrier of the invention, via their carbohydrate moieties. Provided that the carbohydrate moiety is not in the hypervariable region or at the antibody binding sites, the conjugation via the cross-linking with the carbohydrate will not affect binding, as the binding sites will still be available to bind to cell surface antigens.

Methods for making derivatives of sugar ring moieties to create hydrazide groups for coupling with fragments (and antibodies) have been established. See Rodwell, J. D. et al., *Proc. Natl. Acad. Sci. U.S.A*. 83:2632 (1986). Several immunoconjugates prepared in this way are in clinical studies or pending approval for routine clinical uses.

One preferred way to couple binding molecules of the invention (other than Fv fragments) to a polymer backbone, a liposome, or a microbead is to conjugate them through the carbohydrate moiety on the constant regions. For most antibodies, the carbohydrate side chains are on the Fc portion of the antibody molecule. This will maximize the binding sites which are available and not hindered for binding to the antigens. The conjugation through the Fc will also hamper the binding molecule's ability to effect ADCC and complement-mediated cytolytic mechanisms, which is desirable for carrying out the purposes of the invention. As another alternative for use in the invention, antibody molecules with site-specific mutations in the Fc region, so that they do not effect ADCC or complement mediated cytolysis or do not do so to any substantial extent, can be prepared. Alegre, M. L. et al., *J. Immunol*. 148:3461–68 (1992). These modified antibody molecules are also acceptable for use in the invention.

The polymers for conjugating to the binding molecules can be modified to generate active groups for coupling according to established methods. For example, one can make derivatives of PEG with 1,1-carbonyldiamidazole to form imidazole carbamate active groups, which react with amino groups of proteins. Beauchamp, C. O. et al., *Anal. Biochem*. 131:25 (1983). The PEG molecules of the present invention are formed by cross-linking PEG molecules that are regularly used for modifying single protein molecules. These cross-linked PEG molecules are large enough so that a large number of binding molecules can be conjugated to each single PEG molecule. Similar reactions can be used for derivatizing agarose. Bethell, G. S. et al., *J. Biol. Chem*. 254:2572 (1979). The latex beads which are purchased from Interfacial Dynamics Corporation (Portland, Oreg.) are premodified to contain activated groups for coupling with proteins.

The binding molecules can be coupled directly to the derivatized, activated polymers. Bifunctional cross-linkers suitable for conjugating the activated polymers (or liposomes or microbeads) and the binding molecules, can be selected based on the properties desired and the specific substances to be cross-linked. These heterobifunctional reagents are available from several commercial sources, e.g., Pierce Chemical Co., Rockford, Ill., and the reaction procedures are well-known. Wong, S. S., *Chemistry of Protein Conjugation and Cross-Linking*, (CRC Press, Boca Raton, Fla. 1991).

The immunoconjugates of the invention are administered together with an immunogen of interest to generate antibodies against that immunogen. One can immunize rats, mice, primates (or even a human being) with these substances. For preparing MAbs the resulting B cells, or the hybridomas which result following fusion of the B cells with myeloma cells, are screened against the immunogen, or a peptide portion of interest from the immunogen, to isolate the cells of interest. A preferred protocol for preparing MAbs is to fuse immune spleen cells of mice with non-secreting mouse myeloma cells, such as NS-1, SP2/0 or NSO cells using polyethylene glycol.

A preferred immunization protocol for preparing antibodies is to inject into each mouse 50 μg of the conjugate of keyhole limpet hemocyanin and the immunogen together with the immunoconjugates of the invention, rather than CFA, as one would normally use. Four and six weeks later, the same amount of antigen is given subcutaneously in saline. After about eight weeks, the fourth antigen injection is given intraperitoneally in saline. Mice are sacrificed 4 days after the last injection and the spleens are removed for preparing single cell suspensions for fusion with myeloma cells.

EXAMPLE 1

Conjugates of the Invention as Adjuvants for Producing Antibodies

Conjugates of the invention were made by conjugating whole IgG molecules or F(ab')$_2$ fragments of the hamster monoclonal antibody 145-2C11, which is specific for murine CD3-ε chain, onto latex microbeads. The latex beads (of a uniform 2.5 μm diameter, purchased from Interfacial Dynamics Corporation (Portland, Oreg.)), were glutaraldehyde modified. These beads were already modified to contain activated groups for coupling with proteins. Suspensions of these beads could be made homogeneous and suitable for injection with gentle shaking. 5 μg of 145-2C 11.IgG, or 3 μg of 145-2C 11.F(ab')$_2$, were conjugated onto 1 mg of the activated latex beads.

Mice were injected intravenously (via their tail vein) with 50 μg of chimeric human/mouse IgE (hu ε,κ/mu $V_H$, $V_L$) produced by SE44 cells (see Sun L. K. et al., *J. Immunol*. 146:199–205 (1991)), alone and together with, respectively, 145-2C11.IgG (which is designated by "X.IgG" in FIG. 1), and beads conjugated with 145-2C11.IgG (designated "X.IgG/beads"). Mice were also injected intraperitoneally with the chimeric human/mouse IgE together with complete Freund's adjuvant. As controls, beads and X.IgG/beads were also injected intravenously. The murine IgG response was then measured after 14 days.

The mice receiving the X.IgG/beads and chimeric human/ mouse IgE had a much stronger IgG antibody response to the IgE than the mice which received only chimeric human/ mouse IgE. See FIG. 1 ("huIgE" is the chimeric human/ mouse IgE). The response of the mice receiving X.IgG/ beads and chimeric human/mouse IgE was comparable to that of the mice receiving chimeric human/mouse IgE and CFA. See FIG. 1. Mice receiving soluble X.IgG with chimeric human/mouse IgE did not make a detectable antibody response, nor did mice receiving only the X.IgG/beads or only the beads.

These studies demonstrate that the immunoconjugates of the invention are effective adjuvants in increasing the antibody response against an immunogen. The increased response can be exploited and used in production of antibodies and MAbs.

As noted above, the invention is not limited to anti-CD3 binding molecules, such as antibodies and fragments, but also includes binding molecules, fragments (and conjugates thereof) which are specific for surface antigens of human T lymphocytes, and which have immunoregulatory activities in vivo, when administered according to the techniques of the invention. As is true for anti-CD3, many of these in vivo effects would not be predicted from the known in vitro effects or the in vivo effects with the whole antibodies. The desirable stimulatory effects of such products that are prepared according to the present invention will result even though the in vivo effects of IgG specific for T cells are primarily cytolytic effects mediated by complement, ADCC, or other cytolytic mechanisms. In addition to anti-CD3, other examples of antibodies which initiate these cytolytic effects in vivo are anti-CD4 antibodies, Alters, S. E., et al., *J. Immunol.* 144:4587 (1990). All of these antibodies cause T cell depletion in vivo.

Anti-CD4 has been found to have stimulatory effects in vitro. This indicates that, like anti-CD3, when formulated into conjugates of the invention, they would activate or modulate their respective target cells in vivo. A number of studies have indicated that the activation of T cells with an anti-CD3 MAb can be enhanced by an MAb which is specific for a different surface antigen on T cells. These auxiliary MAbs include those specific for HLA class-1 antigens, HLA class-II antigens (such as Ia), CD2, CD4, CD5, CD8, CD28, or CD37. Ceuppens, J. L. et al., *J. Immunol.* 137:1816 (1986); Tutt, A. et al., *J. Immunol.* 147:60 (1991). Thus, the binding molecules which target these antigens, whether used in separate conjugates or in combination with conjugates which include anti-CD3 binding molecules, may be conjugated to microbeads or polymers and used as conjugates of the invention. Some of these antigens, such as CD2, CD4, CD5, and CD8 are specifically expressed by T cells or subsets of T cells. Thus, in one embodiment of the invention, an anti-CD3 binding molecule and an anti-CD2, anti-CD4, anti-CD5, anti-CD8, anti-CD28 or other binding molecule specific for T cells, is conjugated to a polymer backbone, a liposome, or a microbead. The polymerized or immobilized pairs of binding molecules will activate the T cells in vivo, which will induce the enhanced antibody response, meaning that more of the B cells are producing antibodies against the administered immunogen.

It should be understood that the terms and expressions described herein are exemplary only and not limiting, and that the scope of the invention is defined only in the claims which follow, and includes all equivalents of the subject matter of those claims.

What is claimed is:

1. A conjugate comprising a substantially nonimmunogenic polymer coupled with a plurality of binding molecules, each being specific for an antigen on a T cell, and said binding molecules lacking an Fc portion.

2. A conjugate of claim 1, wherein the binding molecule is selected from the group consisting of Fv, Fab, and F(ab')$_2$ fragments.

3. A conjugate of claim 1, wherein the antigen is CD2, CD3, CD4, CD5, CD8, CD28, or a component associated with T cell receptor.

4. A conjugate of claim 1, wherein the nonimmunogenic polymer is nonimmunogenic in humans and resistant to hydrolysis in human body fluids.

5. A conjugate of claim 1, wherein the nonimmunogenic polymer is polyethylene glycol, cellulose, dextran, agarose, latex, or an amino acid copolymer.

6. A conjugate of claim 4, wherein the nonimmunogenic polymer is in the form of a glutaraldehyde modified latex microbead.

7. An improved method for producing antibodies against an immunogen, comprising administering the conjugate of claim 1 to a host animal together with the immunogen and thereby increasing the immunogenic response against the antigen, and screening for antibodies, or cells producing antibodies, which are specifically reactive with the immunogen.

* * * * *